United States Patent [19]

Ueda et al.

[11] Patent Number: 4,613,608
[45] Date of Patent: Sep. 23, 1986

[54] MONO OR DINITROXYALKYL PYRIDINES AND VASODILATING COMPOSITIONS

[75] Inventors: Ikuo Ueda, Uenohigashi; Daizo Morino, Higashishinmachi; Koichi Takimoto, Osaka, all of Japan

[73] Assignee: Fujisawa Pharmaceutical Co., Ltd., Osaka, Japan

[21] Appl. No.: 731,893

[22] Filed: May 8, 1985

Related U.S. Application Data

[62] Division of Ser. No. 515,653, Jul. 20, 1983, Pat. No. 4,540,701.

[30] Foreign Application Priority Data

Jul. 26, 1982 [GB] United Kingdom ............... 8221592

[51] Int. Cl.4 .................. C07D 213/53; A61K 31/44
[52] U.S. Cl. ..................................... 514/357; 546/338
[58] Field of Search ......................... 546/338; 514/357

[56] References Cited

U.S. PATENT DOCUMENTS 3,275,642  9/1966  Broh-Kahn ..................... 546/338
3,689,494  9/1972  Simpson ......................... 546/338

Primary Examiner—Henry R. Jiles
Assistant Examiner—Dale A. Bjorkman
Attorney, Agent, or Firm—Oblon, Fisher, Spivak, McClelland & Maier

[57] ABSTRACT

Compounds of the formula

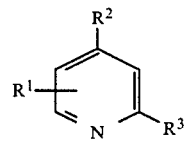

are disclosed wherein
$R^1$ is hydrogen or lower alkyl, one of $R^2$ and $R^3$ is mono (or di)-nitroxy(lower)alkyl and the other
$R^2$ and $R^3$ is hydrogen and pharmaceutically acceptable salts thereof.

Also disclosed are vasodilating compositions containing the above.

8 Claims, No Drawings

MONO OR DINITROXYALKYL PYRIDINES AND VASODILATING COMPOSITIONS

This is a division of application Ser. No. 515,653, filed July 20, 1983, now U.S. Pat. No. 4,540,701.

This invention relates to pyridylalkyl nitrate compound and a salt thereof. More particularly, it relates to a new pyridylalkyl nitrate compound and a pharmaceutically acceptable salt thereof which have vasodilating activities, to process for the preparation thereof, and to a pharmaceutical composition comprising the same for therapeutical treatment of cardiovascular disorder in human being.

With regard to the states of the arts in this field, for example, the following pyridylalkyl nitrate compound is known.

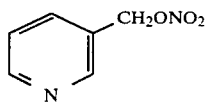

(U.S. Pat. No. 3,275,642.)

One object of this invention is to provide the new and useful pyridylalkyl nitrate compound and a pharmaceutically acceptable salt thereof, which have stronger activity as compared with the known compounds, for example, as shown above.

Another object of this invention is to provide process for the preparation of said pyridylalkyl nitrate compound and the salt thereof.

A further object of this invention is to provide a useful pharmaceutical composition comprising, as an active ingredient, said pyridylalkyl nitrate compound or the pharmaceutically acceptable salt thereof, which is useful, as a vasodilator agent.

Still further object of this invention is to provide a therapeutical method for treatment of cardiovascular disorder such as coronary insufficiency, angina pectoris or myocardial infarction.

The pyridylalkyl nitrate compound of this invention can be represented by the following formula:

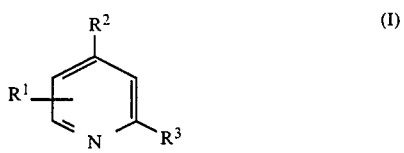

wherein
$R^1$ is hydrogen, lower alkyl, halogen or nitroxy(lower)alkyl,
one of $R^2$ and $R^3$ is mono (or di)-nitroxy(lower)alkyl and
the other of $R^2$ and $R^3$ is hydrogen or halogen.

According to this invention, the object compound (I) can be prepared by the process as illustrated by the following scheme.

Process

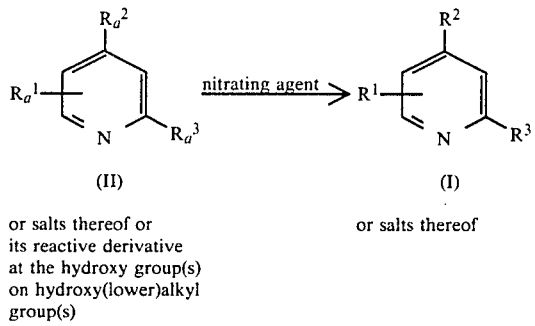

or salts thereof or its reactive derivative at the hydroxy group(s) on hydroxy(lower)alkyl group(s)

or salts thereof wherein
$R^1$, $R^2$ and $R^3$ are each as defined above,
$R_a^1$ is hydrogen, lower alkyl, halogen or hydroxy(lower)alkyl,
one of $R_a^2$ and $R_a^3$ is mono (or di)-hydroxy(lower)alkyl and the other of $R_a^2$ and $R_a^3$ is hydrogen or halogen.

Suitable pharmaceutically acceptable salts of the object compounds (I) are conventional non-toxic salt and include an acid addition salt such as an organic acid salt (e.g. acetate, trifluoroacetate, maleate, tartrate, methanesulfonate, benzenesulfonate, formate, toluenesulfonate, etc.), an inorganic acid salt (e.g. hydrochloride, hydrobromide, hydroiodide, sulfate, nitrate, phosphate, etc.), or a salt with an amino acid (e.g. arginine, aspartic acid, glutamic acid, etc.), or the like.

In the above and subsequent descriptions of the present specification, suitable examples and illustrations of the various definitions which the present invention include within the scope thereof are explained in details as follows.

The term "lower" is intended to mean 1 to 6 carbon atoms, unless otherwise indicated.

Suitable "lower alkyl" and "lower alkyl" moiety in the terms "nitroxy(lower)alkyl", "mono (or di)-nitroxy(lower)alkyl", "hydroxy(lower)alkyl" and "mono (or di)-hydroxy(lower)alkyl" is one having 1 to 6 carbon atom(s) and may include methyl, ethyl, propyl, isopropyl, butyl, isobutyl, tert-butyl, pentyl, tert-pentyl, hexyl and the like, and preferably one having 1 to 4 carbon atom(s).

Suitable halogen may include chlorine, bromine, fluorine and iodine.

Suitable reactive derivative at the hydroxy group(s) on "hydroxy(lower)alkyl" and "mono (or di)-hydroxy(lower)alkyl" may include an acid residue such as halogen as mentioned above or the like.

Process for the preparation of the pyridylalkyl nitrate compound (I) is explained in detail in the following.

A compound (I) or salts thereof can be prepared by reacting a compound (II) or salts thereof or its reactive derivative at the hydroxy group(s) on hydroxy(lower)alkyl group(s) with a nitrating agent.

Suitable salts of the compound (II) can be referred to the ones as exemplified for the compound (I).

Suitable nitrating agent used in the process may include nitric acid, a combination of acetic anhydride and nitric acid or a combination of concentrated sulfuric acid and nitric acid, or the like.

The reaction temperature is not critical and the reaction is usually carried out under cooling or at ambient temperature. The reaction is usually carried out without solvent or in a solvent such as acetic acid or other conventional solvents which do not adversely affect the reaction.

Thus obtained compound (I) may be converted into pharmaceutically acceptable salts thereof by conventional manner.

For therapeutical purpose, the pyridylalkyl nitrate compound (I) is administered in daily dose of 0.01 to 50 mg, preferably 0.1 to 10 mg.

The pharmaceutical compositions of this invention comprise, as an active ingredient, the pyridylalkyl nitrate compound (I) or pharmaceutically acceptable salt thereof in an amount of about 0.01 mg to about 10 mg, preferably about 0.01 mg to about 5 mg per dosage unit for oral and parenteral use.

One skilled in the art will recognize that the amount of the active ingredient in the dosage unit form may be determined by considering the activity of the ingredient as well as the size of the host human being. The active ingredient may usually be formulated in a solid form such as tablet, granule, powder, capsule, troche, lozenge or suppository, or a suspension or solution form such as syrup, injection, emulsion, lemonade, etc. and the like.

A pharmaceutical carrier or diluent includes solid or liquid non-toxic pharmaceutically acceptable substances. Examples of solid or liquid carriers or diluents are lactose, magnesium stearate, terra alba, sucrose, corn starch, talc, stearic acid, gelatin, agar, pectin, acacia, peanut oil, olive oil or sesame oil, cacao butter, ethyleneglycol or the other conventional ones. Similarly, the carrier or diluent may include a time delay material such as glyceryl monostearate, glyceryl distearate, a wax and the like.

For the purpose of showing the utility of the compound (I), the pharmacological test results of some representative compounds are shown as follows.

EFFECT ON ISOLATED CORONARY ARTERY

Test Method

The large and small coronary arteries, 2.0 and 0.5 mm in outside diameter respectively, were removed from pentobarbital-anesthetized dogs. Spiral strips approximately 15 and 5 mm in length were cut from the large and small arteries respectively, and suspended in an organ bath containing Tyrode's solution at 37° C., aerated with a gas mixture of 95% oxygen and 5% carbon dioxide. The tonus of the strips was recorded on a polygraph with a force-displacement transducer. After the initial resting tension was adjusted to 1.0 g for the large artery and 100 mg for the small artery, potassium chloride 35 mM was added to the organ bath to increase the tonus of the large arterial strips to 1.4–1.6 g and the small arterial strips to 120–140 mg. The cumulative concentrations of the test compounds were then added, and finally papaverine $10^{-4}$M was given to determine maximum relaxation. $ED_{50}$ values were calculated by interpolation from the mean cumulative dose-activity curves (effect of papaverine $10^{-4}$M = 100%).

Test Compound

Compound A: 3-Nitroxymethylpyridine (reference compound)
Compound B: 2,6-Bis(nitroxymethyl)pyridine
Compound C: 4-(3-Nitroxypropyl)pyridine
Compound D: 2-Nitroxymethyl-6-chloropyridine
Compound E: 2,6-Bis(nitroxymethyl)-4-chloropyridine Test Results The values are shown in the following Table.

As clear from the test results in the Table, especially from S/L values, it is evident that the compounds of the present invention is characterized by possessing potent and selective dilating activity on large coronary artery as compared with small coronary artery, which means that the compounds of the present invention are useful for treatment of cardiovascular disorder.

| Compound | $ED_{50}$ g/ml Large (L) | Small (S) | S/L |
|---|---|---|---|
| A | $8.0 \times 10^{-8}$ | $1.9 \times 10^{-6}$ | 23.8 |
| B | $4.0 \times 10^{-9}$ | $2.25 \times 10^{-7}$ | 56.3 |
| C | $1.25 \times 10^{-8}$ | $>1.0 \times 10^{-5}$ | >800 |
| D | $6.7 \times 10^{-9}$ | $6.2 \times 10^{-6}$ | 925 |
| E | $2.75 \times 10^{-9}$ | $2.30 \times 10^{-7}$ | 83.6 |

The following Examples are given for the purpose of illustrating the present invention.

Preparation of the object compounds for this invention:

EXAMPLE 1

Fuming nitric acid (4.1 ml) was added dropwise to acetic anhydride (13.5 ml) with stirring at 5° to 10° C. After the mixture was stirred for 30 minutes at 5° C., 2-hydroxymethylpyridine nitrate (3.3 g) was added in some portions thereto. The resulting mixture was stirred for 3 hours at 0° to 5° C. A mixture of benzene (15 ml) and n-hexane (30 ml) was added thereto. The mixture formed two layers. The upper layer was separated and discarded while the remaining lower layer was again treated with a mixture of benzene (10 ml) and n-hexane (10 ml). After the separation of the layers, the lower layer was again separated, mixed with benzene (10 ml) and made homogeneous with isopropyl alcohol (10 ml). The resulting mixture was allowed to stand overnight in a refrigerator to give crystals. The crystals were collected by filtration and washed with diethyl ether to give white crystals of 2-nitroxymethylpyridine nitrate (2.4 g), mp. 75° to 77° C.

IR (Nujol): 2450, 2050, 1645, 1430, 1280, 840 cm$^{-1}$.
NMR (DMSO-$d_6$, δ): 5.85 (2H, s), 7.65–8.1 (2H, m), 8.1–8.5 (1H, m), 9.85 (1H, dd, J=5.5 Hz, 1 Hz), 14.95 (1H, s).

Analysis for $C_6H_6N_2O_3 \cdot HNO_3$: Calcd.: C: 33.19, H: 3.25, N: 19.35. Found: C: 32.86, H: 3.17, N: 19.31.

EXAMPLE 2

Fuming nitric acid (5 ml) was added dropwise to acetic anhydride (9.5 ml) with stirring at 5° to 10° C. 2,6-Bis(hydroxymethyl)pyridine (6.95 g) was added thereto. The resulting mixture was stirred for 20 minutes at 5° to 10° C. and for additional 1.5 hours at 20° C., and then poured into a mixture of ethyl acetate (40 ml) and ice-water (60 ml). The resulting mixture was neutralized with aqueous potassium carbonate solutions. The ethyl acetate layer was separated, washed with water, dried over anhydrous magnesium sulfate, and concentrated under reduced pressure. The residue obtained was subjected to column chromatography on aluminum oxide (30 g) and eluted with toluene. The fractions containing the desired compound were concentrated under reduced pressure to give colorless viscous oil of 2,6-bis(nitroxymethyl)pyridine (5.1 g).

IR (Nujol): 1635, 1600, 1460, 1285, 1160, 970, 850 cm$^{-1}$.

NMR (CDCl$_3$, δ): 5.50 (4H, s), 2.34 (2H, d, J=8 Hz), 7.78 (1H, t, J=8 Hz).

Analysis for C$_7$H$_7$N$_3$O$_6$: Calcd.: C: 36.69, H: 3.08, N: 18.34. Found: C: 36.97, H: 3.16, N: 18,64.

EXAMPLE 3

The following compounds were obtained according to similar manners to those of Examples 1 and 2.

(1) 2-(2-Nitroxyethyl)pyridine nitrate, mp. 49°–52° C.

IR (Nujol): 2560, 2110, 1635, 1625, 1405, 1315, 1280 cm$^{-1}$.

NMR (DMSO-d$_6$, δ): 3.51 (2H, t, J=6 Hz), 4.99 (2H, t, J=6 Hz), 7.8–8.3 (2H, m), 8.59 (1H, dt, J=8 Hz, 2 Hz), 8.93 (1H, dd, J=6 Hz, 2 Hz), 13.45 (1H, s).

Analysis for C$_7$H$_8$N$_2$O$_3$.HNO$_3$: Calcd.: C: 36.37, H: 3.92, N: 18.18. Found: C: 35.97, H: 3.86, N: 18.19.

(2) 2-(1-Nitroxymethyl-2-nitroxyethyl)pyridine hydrochloride, mp. 111°–112° C.

IR (Nujol): 2420, 1620, 1460, 1275, 990, 870, 840, 750 cm$^{-1}$.

NMR (DMSO-d$_6$, δ): 2.32 (1H, quintet, J=6 Hz), 5.14 (4H, d, J=6 Hz), 7.90 (1H, m), 8.14 (1H, d, J=8 Hz), 8.47 (1H, dt, J=8 Hz, 2 Hz), 8.87 (1H, dd, J=4 Hz, 2Hz), 18.20 (1H, brs).

Analysis for C$_8$H$_9$N$_3$O$_6$.HCl: Calcd.: C: 34.36, H: 3.60, N: 15.03, Cl: 12.68. Found: C: 34.13, H: 3.61, N: 14.78, Cl: 12.50.

(3) 2,6-Bis(nitroxymethyl)-4-chloropyridine, mp. 30°–35° C. IR (Nujol): 1638, 1582, 1278, 1043, 847, 756 cm$^{-1}$.

NMR (CDCl$_3$, δ): 5.52 (4H, s), 7.35 (2H, s). Analysis for C$_7$H$_6$ClN$_3$O$_6$: Calcd.: C: 31.89, H: 2.29, N: 15.94. Found: C: 32.06, H: 2.29, N: 16.12.

(4) 4-(3-Nitroxypropyl)pyridine.

IR (Nujol): 1625, 1410, 1275, 865, 800, 760 cm$^{-1}$.

NMR (CCl$_4$, δ): 1.7–2.4 (2H, m), 2.73 (2H, t, J=7 Hz), 4.41 (2H, t, J=7 Hz), 7.03 (2H, d, J=5 Hz), 8.39 (2H, d, J=5 Hz).

Analysis for C$_8$H$_{10}$N$_2$O$_3$: Calcd.: C: 52.74, H: 5.53, N: 15.38. Found: C: 53.19, H: 5.64, N: 15.30.

(5) 2-Nitroxymethyl-6-methylpyridine hydrochloride, mp. 65°–68° C.

IR (Nujol): 1635, 1275, 1171, 999, 847, 837 cm$^{-1}$.

NMR (CCl$_4$, δ free form): 2.48 (3H, s), 5.40 (2H, s), 7.02 (1H, d, J=8 Hz), 7.04 (1H, d, J=8 Hz), 7.49 (1H, t, J=8 Hz).

Analysis for C$_7$H$_8$N$_2$O$_3$.HCl: Calcd.: C: 41.09, H: 4.43, N: 13.69. Found: C: 40.80, H: 4.42, N: 13.68.

(6) 2-Nitroxymethyl-6-chloropyridine

IR (Nujol): 1636, 1585, 1563, 1439, 1281, 1160, 1138, 985, 846, 785 cm$^{-1}$.

NMR (CCl$_4$, δ): 5.47 (2H, s), 7.15–7.45 (2H, m), 7.69 (1H, dd, J=8.5 Hz, J=6 Hz).

Analysis for C$_6$H$_5$ClN$_2$O$_3$: Calcd.: C: 38.22, H: 2.67, N: 14.86. Found: C: 37.97, H: 2.75, N: 14.95.

What we claim is:

1. A pyridylalkyl nitrate compound of the formula:

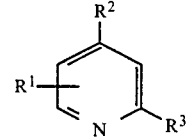

wherein
R$^1$ is hydrogen or lower alkyl,
one of R$^2$ and R$^3$ is mono (or di)-nitroxy(lower)alkyl and the other of R$^2$ and R$^3$ is hydrogen,
and pharmaceutically acceptable salts thereof.

2. The compound of claim 1, wherein
R$^1$ is hydrogen or methyl, one of R$^2$ and R$^3$ is nitroxymethyl, 2-nitroxyethyl, 3-nitroxypropyl or 1-nitroxymethyl-2-nitroxyethyl and the other of R$^2$ and R$^3$ is hydrogen.

3. The compound of claim 2, which is 2-nitroxymethylpyridine or its nitrate.

4. The compound of claim 2, which is 2-(2-nitroxyethyl)pyridine or its nitrate.

5. The compound of claim 2, which is 2-(1-nitroxymethyl-2-nitroxyethyl)pyridine or its hydrochloride.

6. The compound 4-(3-nitroxypropyl)pyridine.

7. The compound of claim 2, which is 2-nitroxymethyl-6-methylpyridine or its hydrochloride.

8. A vasodilating, pharmaceutical composition comprising an effective amount of a compound of claim 1 or pharmaceutically acceptable salt thereof in association with a pharmaceutically acceptable, substantially non-toxic carrier or excipient.

* * * * *